United States Patent [19]

Pawelchak et al.

[11] 4,393,080

[45] Jul. 12, 1983

[54] ADHESIVE COMPOSITIONS

[75] Inventors: John M. Pawelchak, East Windsor; James L. Chen, East Brunswick; John G. Cryan, East Brunswick; Anthony L. LaVia, East Brunswick, all of N.J.

[73] Assignee: E. R. Squibb & Sons, Inc., Princeton, N.J.

[21] Appl. No.: 334,284

[22] Filed: Dec. 24, 1981

[51] Int. Cl.$^3$ .............................. C09J 7/02; B32B 9/00
[52] U.S. Cl. ..................................... 428/355; 428/356; 428/424.2; 428/447; 428/451; 428/476.6; 428/478.2; 428/492; 428/516; 428/520; 523/111; 523/118; 524/17; 524/22; 524/37; 524/55; 525/389
[58] Field of Search .................. 523/111, 118; 524/17, 524/22, 37, 55; 428/424.2, 492, 516, 355–356, 447, 451, 476.6, 478.2, 520; 525/389; 128/283; 3/1

[56] References Cited

U.S. PATENT DOCUMENTS

| | | | |
|---|---|---|---|
| 3,302,647 | 2/1967 | Marsan | 128/283 |
| 3,339,546 | 9/1967 | Chen | 128/156 |
| 3,568,675 | 3/1971 | Harvey | 128/275 |
| 3,589,364 | 6/1971 | Dean et al. | 128/284 |
| 3,612,053 | 10/1971 | Pratt | 128/283 |
| 3,640,741 | 2/1972 | Etes | 128/283 |
| 3,661,815 | 5/1972 | Smith | 260/174 |
| 3,667,469 | 6/1972 | Marsan | 128/283 |
| 3,712,304 | 1/1973 | Marsan | 128/283 |
| 3,713,445 | 1/1973 | Marsan | 128/283 |
| 3,799,166 | 3/1974 | Marsan | 128/283 |
| 3,835,857 | 9/1974 | Rogers et al. | 128/295 |
| 3,863,638 | 2/1975 | Rogers et al. | 128/295 |
| 3,876,771 | 4/1975 | Denner | 424/78 |
| 3,877,431 | 4/1975 | Kross | 128/283 |
| 3,908,658 | 9/1975 | Marsan | 128/283 |
| 3,954,105 | 5/1976 | Nordby | 128/275 |
| 3,980,084 | 9/1976 | Kross | 128/283 |
| 4,007,263 | 2/1977 | Pichierri | 424/78 |
| 4,078,568 | 3/1978 | Etes et al. | 128/283 |
| 4,123,409 | 10/1978 | Kaelble | 523/118 |
| 4,153,055 | 5/1979 | Etes | 128/283 |
| 4,166,051 | 8/1979 | Cilento et al. | 524/55 |
| 4,192,785 | 3/1980 | Chen | 523/118 |
| 4,198,979 | 4/1980 | Cooney et al. | 128/295 |
| 4,231,369 | 1/1980 | Sorensen et al. | 128/283 |
| 4,253,460 | 3/1981 | Chen et al. | 128/283 |

FOREIGN PATENT DOCUMENTS 1571657  7/1980  United Kingdom .

OTHER PUBLICATIONS

GAF, "Toxicity Studies on the Gantrez Series of PVM/MA Copolymers".
Chen et al., Adhesion in Biological Systems, (1970), Chapter 10, pp. 163–181.
Shell, Kraton, pp. 1–6.
GAF, Chemical Catalogue, pp. 38–40.

*Primary Examiner*—Lucille M. Phynes
*Attorney, Agent, or Firm*—Lawrence S. Levinson; Stephen B. Davis

[57] ABSTRACT

Medical grade adhesive compositions comprising a homogeneous blend of one or more pressure sensitive adhesive materials and one or more natural or synthetic polymers capable of developing elastomeric properties when hydrated such as gluten and long chain polymers of methyl vinyl ether/maleic acid are disclosed. The compositions may also include one or more water soluble hydrocolloid gums and may additionally contain one or more water swellable cohesive strengthening agents.

31 Claims, 2 Drawing Figures

ADHESIVE COMPOSITIONS

BACKGROUND OF THE INVENTION

Various adhesive compositions suitable for medical use and in particular adapted to be used with ostomy appliances have been disclosed in the patent literature.

Chen in U.S. Pat. No. 3,339,546 discloses an adhesive composition comprising a blend of one or more water soluble or water swellable hydrocolloids and a viscous substance such as polyisobutylene. The adhesive mass has a film of water insoluble material affixed to one surface. Such a bandage is commercially available under the trademark Stomahesive from E. R. Squibb & Sons, Inc. and is employed as a skin barrier by ostomates.

Chen et al. in U.S. Pat. No. 4,192,785 describe an adhesive composition suitable for use with an ostomy appliance consisting of a mixture of one or more hydrocolloid gums, a pressure sensitive adhesive such as one or more polyisobutylenes, and a cohesive strengthening agent. The cohesive strengthening agent can be a natural or synthetic fibrous material, finely divided cellulose, cross-linked dextran, cross-linked carboxymethylcellulose, or a starch-acrylonitrile graft copolymer.

Other types of adhesive products suggested for use by ostomates include a pad of a gel of karaya and glycerol as taught by Marsan in U.S. Pat. No. 3,302,647. Pratt in U.S. Pat. No. 3,612,053 discloses an ostomy sealing washer containing styrene isoprene and styrene butadiene block copolymers. Etes in U.S. Pat. No. 3,640,741 discloses an ostomy sealing washer prepared by cross-linking a hydrophilic colloid such as carboxymethylcellulose with a polyol such as propylene glycol. Sealing rings containing starch are disclosed by Marsan in U.S. Pat. Nos. 3,667,469, 3,712,304 and 3,799,166 and rings made of an open cell foam are disclosed by Marsan in U.S. Pat. No. 3,713,445. Marsan in U.S. Pat. No. 3,908,658 discloses a sealing ring consisting of a mixture of mineral oil, styreneisobutylene copolymer and ethylene-vinyl acetate copolymer. Kross in U.S. Pat. Nos. 3,877,431 and 3,980,084 disclose an ostomy sealing gasket consisting of a polymer made from reacting a hydroxyalkyl acrylate or methacrylate with a polyalkylene glycol in the presence of a reducing agent and water. Etes et al. in U.S. Pat. No. 4,078,568 and Etes in U.S. Pat. No. 4,153,055 disclose ostomy sealing gaskets containing an acrylamide-beta methacryloxyethyl trimethyl ammonium sulfate copolymer. Sorensen et al. in U.S. Pat. No. 4,231,369 discloses sealing material comprising one or more hydrocolloids and a hydrocarbon tacifier dispersed in a styrene-olefin-styrene or ethylene-propylene block copolymer.

Denner in U.S. Pat. No. 3,876,771 discloses a protective skin coating of gelatinous material made up of a film-forming protective colloid material in combination with a solvent and a gelling agent. The film former is a monoisopropyl ester of polyvinyl methylether/maleic acid.

Pichierri in U.S. Pat. No. 4,007,263 discloses a method of relieving skin irritation around a stoma by applying a paste composition containing at least 40 percent of a calcium, sodium poly(vinylmethylether/maleate) in a petroleum base.

Cilento et al. in U.S. Pat. No. 4,166,051 discloses a putty-like composition for use around a stoma consisting of a homogeneous mixture of a pressure sensitive adhesive component such as polyisobutylene, mineral oil, and hydrocolloid gums or cohesive strengthening agents or mixtures thereof.

SUMMARY OF THE INVENTION

Figure 1:
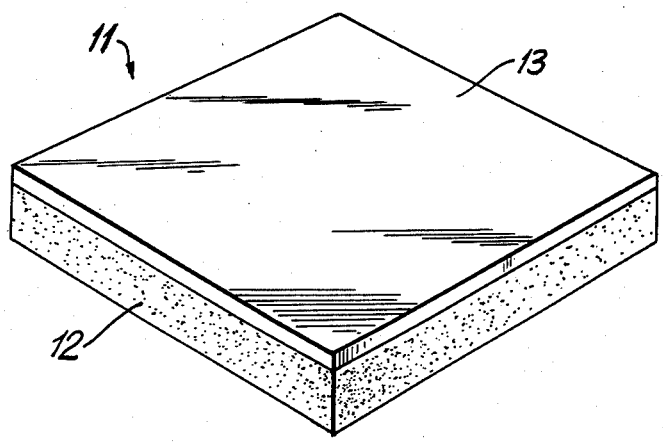
FIG. 1 is a perspective view of a skin barrier incorporating the adhesive composition of this invention.

This invention is directed to an adhesive composition particularly adapted to be used in the ostomy care field.

The adhesive compositions are a homogeneous blend of one or more pressure sensitive adhesive materials and one or more natural or synthetic polymers capable of developing elastomeric properties when hydrated such as gluten and long chain polymers of methyl vinyl ether/maleic acid. The composition may also include one or more water soluble hydrocolloid gums and may additionally contain one or more water swellable cohesive strengthening agents. Additionally, one or more thermoplastic elastomers may be included with the pressure sensitive adhesive materials.

DETAILED DESCRIPTION OF THE INVENTION

This invention is directed to adhesive compositions suitable for various medical applications and, in particular, suited for use in the field of ostomy care. The adhesive compositions of this invention are resistant to erosion by moisture and biological fluids which are excreted from a stoma and can leak from a collection appliance. Also, the adhesive compositions of this invention are non-irritating to the human skin.

Thus, a skin barrier prepared from the adhesive compositions of this invention or a drainable ostomy pouch having an adhesive faceplate made from the adhesive compositions of this invention can remain in place around the stoma for from several days to a week or longer. This diminishes irritation to the sensitive skin around a stoma resulting from the frequent removal of adhesive skin barriers and also represents a cost savings for the ostomate.

The adhesive composition of this invention comprises a homogeneous blend of one or more pressure sensitive adhesive materials and one or more natural or synthetic polymers capable of developing elastomeric properties when hydrated such as gluten and long chain polymers of methyl vinyl ether/maleic acid. The composition preferably also includes one or more water soluble hydrocolloid gums and may additionally include one or more water swellable cohesive strengthening agents. Additionally, one or more thermoplastic elastomers may be included with the pressure sensitive adhesive materials.

The pressure sensitive adhesive component of the composition provides dry adhesion and holds the entire composition together. Various natural or synthetic viscous or elastomeric substances such as natural rubber, silicone rubber, acrylonitrile rubber, polyurethane rubber, polyisobutylene, etc., either possessing dry tack by themselves or developing such tack upon the addition of a plasticizer are suitable for this purpose. Low molecular weight polyisobutylenes having a viscosity average molecular weight of from about 36,000 to about 58,000 (Flory) possessing pressure sensitive adhesive properties are preferred. Such polyisobutylenes are commercially available under the trademark Vistanex from Exxon as grades LM-MS and LM-MH.

Optionally, one or more thermoplastic elastomers can be included in the pressure sensitive adhesive component. These elastomers impart the properties of rubber-like extensibility and both rapid and complete recovery from modular strains to the pressure sensitive adhesive component. Suitable thermoplastic elastomers include medium molecular weight polyisobutylenes having a viscosity average molecular weight of from about 1,150,000 to 1,600,000 (Florey), butyl rubber which is a copolymer of isobutylene with a minor amount of isoprene having a viscosity average molecular weight of from about 300,000 to about 450,000 (Florey), and styrene copolymers such as styrene-butadiene-styrene (S—B—S), styrene-isoprene-styrene (S—I—S), and styrene-ethylene/butylene-styrene (S—EB—S) which are commercially available, for example, from Shell Chemical Co. under the trademark Kraton as Kraton D1100, D1102, Kraton D1107, Kraton 4000, Kraton G1600, and Kraton G4600. Preferred thermoplastic elastomers are butyl rubber having a viscosity average molecular weight of about 425,000 (commercially available as grade 077), polyisobutylene having a viscosity average molecular weight of about 1,200,000 (commercially available under the trademark Vistanex from Exxon as grade L-100), and styrene-isoprene-styrene (S—I—S) copolymers (commercially available from Shell as Kraton D1107).

The pressure sensitive adhesive component including the optional thermoplastic elastomer is present at from about 30% to about 70% by weight of the composition, preferably from about 40% to about 50% by weight. The thermoplastic elastomer can be employed at up to three times the weight of the pressure sensitive elastomeric substances but preferably the thermoplastic elastomer if present will be at from about 20% to about 40% by weight of the pressure sensitive elastomeric substance.

The natural or synthetic polymers which develop elastomeric properties when hydrated are present at from about 3% to about 60% by weight of the adhesive composition. The preferred materials are the long chain polymers of methyl vinyl ether/maleic acid commercially available under the trademark Gantrez from GAF Inc. The maleic acid moeity in the polymer may be intact (Gantrez S-97), may be an anhydride (Gantrez AN-169), or may be a metal salt such as the mixed sodium/calcium salts (Gantrez AT-955). These materials are hydrophilic and when hydrated form extensible elastic masses with substantial tack to skin and other surfaces.

The adhesive composition may also include up to about 50% by weight of one or more water soluble hydrocolloid gums. Suitable hydrocolloid gums include sodium carboxymethylcellulose, pectin, gelatin, guar gum, locust bean gum, and gum karaya. The adhesive composition may also include up to about 30% by weight of one or more water swellable cohesive strengthening agents provided that the water soluble hydrocolloid gums and water swellable cohesive strengthening agents together are present at no more than about 60% by weight of said adhesive composition. Suitable water swellable cohesive strengthening agents include finely divided substantially water insoluble cross-linked sodium carboxymethylcellulose such as that commercially available under the trademark Aqualon or that described in U.S. Pat. No. 3,589,364 and available commercially from The Buckeye Cellulose Corp., finely divided substantially water insoluble starch-acrylonitrile graft copolymer such as that described in U.S. Pat. No. 3,661,815 and commercially available from the Grain Processing Corp, and finely divided substantially water insoluble cross-linked dextran such as that commercially available under the trademark Sephadex. The water soluble hydrocolloids provide additional wet tack for the adhesive composition and they along with the water swellable cohesive strengthening agents function to control the rate of hydration of the methyl vinyl ether/maleic acid polymeric material.

Preferably, if the adhesive composition contains one or more water soluble hydrocolloid gums then such gums will be present at from about 15% to about 40% by weight of the composition and the combination of the water soluble hydrocolloid gums and water swellable cohesive strengthening agents will be no more than about 55% by weight of the adhesive composition. Also, in these formulas the methyl vinyl ether/maleic acid polymers will be present at from about 10% to about 35% by weight of the adhesive composition.

Small amounts, i.e., less than about 5% by weight of the adhesive composition, of other ingredients may be included in the adhesive composition. For example, a plasticizer such as mineral oil, a tackifying resin such as Piccolyte, an antioxidant such as butylated hydroxyanisole or butylated hydroxytoluene, a deodorant such as chlorophyllins, or a perfume agent may be included. In addition, small amounts of a pharmacologically active ingredient can be included in the adhesive composition. For example, an antibiotic or antimicrobial agent such as neomycin, an antiseptic agent such as povidone iodine, and an antiinflammatory agent such as hydrocortisone or triamcinolone acetonide.

The adhesive compositions are prepared by forming a premix of the gluten or methyl vinyl ether/maleic acid polymeric material, the water soluble hydrocolloid gums, and the cohesive strengthening agents and any other optional substances. The premixed powder is then placed in a heavy duty high shear sigma blade or equivalent type mixer. The viscous pressure sensitive adhesive component is then added in two or three equal segments. Mixing is allowed to proceed for approximately ten minutes between each addition of the viscous material. The resultant dough-like mass is then extruded and rolled or pressed to desired thickness. In working with large batches of material, the dough-like mass may be kneaded prior to the extrusion step. Alternatively, the process may be varied by first working the viscous pressure sensitive adhesive material in the mixer for about ten minutes and then adding the powder premix in two or three equal segments with agitation for about 15 minutes between each addition. When the pressure sensitive adhesive component includes an amount of optional thermoplastic elastomer, such elastomer is first blended by geometric dilution with the pressure sensitive adhesive material in a heated high shear sigma blade or equivalent type mixer.

As shown in FIG. 1, if desired, a thin continuous or discontinuous film 13 of polymeric material such as polyethylene, polypropylene, polyurethane, polyvinylchloride, etc., can be laminated onto one side of the adhesive composition 12 as taught by Chen in U.S. Pat. No. 3,339,546. In the skin barrier 11, the adhesive layer 12 will vary in thickness from about 10 to about 120 mils and the film 13 will vary in thickness from about 1 to about 10 mils. The exposed side of the adhesive composition or both sides if the film is omitted is covered with a piece of silicone coated release paper.

A flange can be affixed to the film 13 for attachment of an ostomy bag as is known in the art. Preferably, a projecting rim shaped coupling member is affixed to film 13 as described by Steer et al. in British Pat. No. 1,571,657. An ostomy bag having a coacting channel shaped coupling member can then be secured to the skin barrier.

Figure 2:
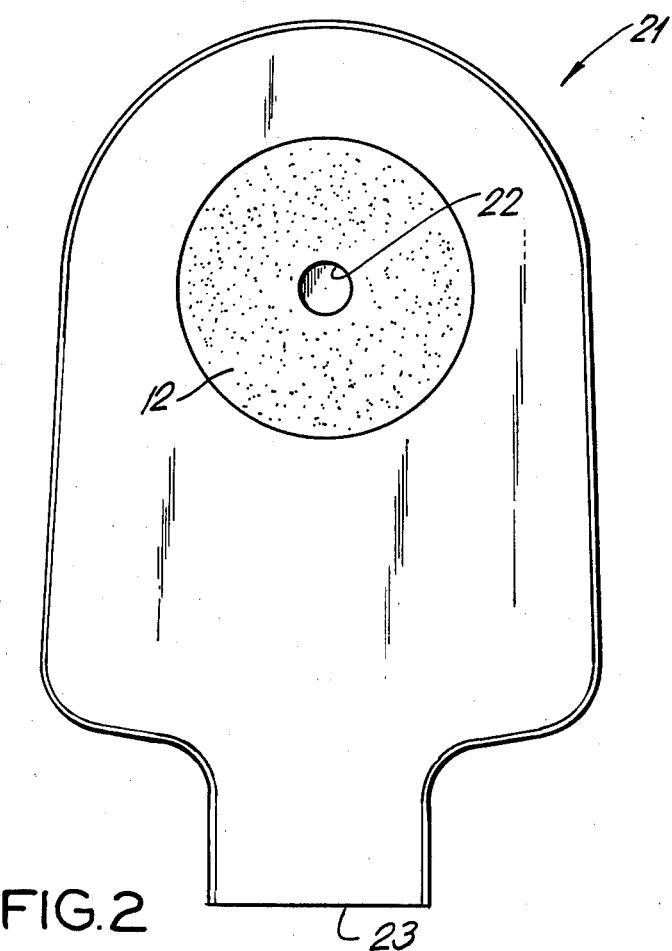
FIG. 2 is a front view of a drainable ostomy pouch having an adhesive faceplate of the composition of this invention.

FIG. 2 shows the adhesive composition 12 affixed as a mounting faceplate on a drainable ostomy pouch 21. The pouch 21 is formed by conventional procedures such as by heat sealing two films or polymeric material around their periphery except for a bottom opening 23. The mounting faceplate and pouch include an opening 22 which is enlarged by the ostomate so as to fit snuggly around the stoma. The drainable opening 23 is closed by a clip as shown in the art. Of course, the adhesive composition 12 may be employed as a faceplate on a disposable ostomy pouch.

While the adhesive compositions of this invention have been particularly described for use in the ostomy field, they are also useful for other medical purposes. For example, the adhesive compositions may be packaged in strip form and employed to hold a male incontinence device in place as described by Rodgers et al. in U.S. Pat. Nos. 3,835,857 and 3,863,638. The adhesive compositions may also be employed to affix various medical devices to the body such as a female incontinence device as described by Cooney et al. in U.S. Pat. No. 4,198,979, a wound drainage system as described by Harvey in U.S. Pat. No. 3,568,675 and by Nordby in U.S. Pat. No. 3,954,105, a catheter, or an electronic probe. The adhesive compositions of this invention can be used on the mucous membrane in the mouth, in the vagina, or in various surgical procedures such as on the surface of an internal organ such as the liver.

The adhesive compositions of this invention may be sterilized by means of gamma radiation.

The following examples are illustrative of the invention. Other suitable adhesive compositions can be obtained by minor variations in the amounts of ingredients employed.

EXAMPLE 1

This example was directed to preparing an adhesive mass having the following composition:

| Ingredient | Percent by weight |
| --- | --- |
| Polyisobutylene (Vistanex LM-MH) | 40 |
| Guar gum | 25 |
| Sodium carboxymethylcellulose | 10 |
| Cross-linked sodium carboxymethylcellulose (Aqualon R) | 15 |
| Sodium, calcium poly(methyl vinyl ether/maleic acid) [Gantrez AT-955] | 10 |
| | 100 |

A premix was prepared by blending 2.5 kg. of finely divided guar gum, 1.0 kg. of sodium carboxymethylcellulose, 1.5 kg. of cross-linked sodium carboxymethylcellulose and 1.0 kg. of sodium, calcium poly(methyl vinyl ether/maleic acid). The blended premix was added to a heavy duty sigma blade-type mixer followed by the addition of 2 kg. of polyisobutylene. After mixing for ten minutes, an additional 2 kg. of polyisobutylene was added and mixing continued until a homogeneous dough was formed (about 10 to twenty minutes).

This dough mass while hot and soft was extruded and flattened. A sheet of polyethylene 1.5 mils thickness was pressed over one side and silicone coated release paper on the other. The resultant mat was cut into the desired shape.

EXAMPLES 2–17

Following the procedure of Example 1 but employing the following ingredients on a weight percent basis other adhesive compositions within the scope of the invention are prepared.

| Ingredient | \multicolumn{8}{c}{Examples} | | | | | | | |
| --- | --- | --- | --- | --- | --- | --- | --- | --- |
| | 2 | 3 | 4 | 5 | 6 | 7 | 8 | 9 |
| Polyisobutylene (Vistanex LM-MH) | 40 | 40 | 40 | 40 | 40 | 45 | 50 | 60 |
| Guar gum | 25 | — | — | 30 | — | — | 30 | 25 |
| Locust bean gum | — | — | — | — | — | 25 | — | — |
| Pectin | — | — | — | — | — | 15 | — | — |
| Karaya | — | — | — | — | — | — | — | — |
| Gelatin | — | — | — | — | — | — | — | — |
| Sodium carboxymethylcellulose | 10 | — | 30 | — | 17.2 | — | — | — |
| Cross-linked sodium carboxymethylcellulose (Aqualon R) | 15 | — | — | — | 25.6 | — | — | — |
| Starch-acrylonitrile graft copolymer (Grain Processing Corp. Polymer 35-A-100) | — | — | — | — | — | — | — | — |
| Cross-linked dextran (Sephadex CM-C50) | — | — | — | — | — | — | — | — |
| Poly(methyl vinyl ether/maleic acid), or its anhydride, or mixed calcium, sodium salt [Gantrez S-97, AN-169, or AT-955] | 10 (S-97) | 60 (AT-955) | 30 (AT-955) | 30 (AT-955) | 17.2 (AT-955) | 15 (AT-955) | 20 (AN-169) | 15 (S-97) |
| Gluten | — | — | — | — | — | — | — | — |

| | 10 | 11 | 12 | 13 | 14 | 15 | 16 | 17 |
| --- | --- | --- | --- | --- | --- | --- | --- | --- |
| Polyisobutylene (Vistanex LM-MH) | 40 | 40 | 40 | 40 | 35 | 40 | 50 | 40 |
| Guar gum | — | 25 | 30 | 30 | 25 | 25 | 20 | 20 |
| Locust bean gum | — | — | — | — | — | — | — | — |
| Pectin | 15 | — | — | — | 15 | — | — | — |
| Karaya | — | 15 | — | — | — | — | — | — |
| Gelatin | 15 | — | — | — | — | — | — | — |
| Sodium carboxymethylcellulose | 15 | — | — | — | — | 10 | 10 | — |
| Cross-linked sodium carboxymethylcellulose | — | 10 | — | — | 7.5 | 10 | 10 | 20 |

-continued

| Ingredient | Examples | | | | | | | |
|---|---|---|---|---|---|---|---|---|
| (Aqualon R) | | | | | | | | |
| Starch-acrylonitrile graft copolymer (Grain Processing Corp. Polymer 35-A-100) | — | — | 10 | — | 7.5 | — | — | — |
| Cross-linked dextran (Sephadex CM-C50) | — | — | — | 10 | — | — | — | — |
| Poly(methyl vinyl ether/maleic acid), or its anhydride, or mixed calcium, sodium salt [Gantrez S-97, AN-169, or AT-955] | 15 (AT-955) | 10 (AT-955) | 20 (AT-955) | 20 (AT-955) | 10 (AT-955) | — | — | — |
| Gluten | — | — | — | — | — | 15 | 10 | 20 |

EXAMPLE 18

This example is directed to preparing an adhesive mass having the following composition:

| Ingredient | Percent by weight |
|---|---|
| Polyisobutylene (Vistanex LM-MH) | 32 |
| Guar Gum | 25 |
| Sodium carboxymethylcellulose | 12 |
| Cross-linked sodium carboxymethylcellulose (Aqualon R) | 13 |
| Sodium, calcium poly(methyl vinyl ether/maleic acid) [Gantrez AT-955] | 10 |
| Styrene-isoprene copolymer (Kraton 1107) | 8 |

A powder premix is prepared by blending 2.5 kg. of finely divided guar gum, 1.2 kg. of sodium carboxymethylcellulose, 1.3 kg. of cross-linked sodium carboxymethylcellulose, and 1.0 kg. of sodium, calcium poly(methyl vinyl ether/maleic acid).

The Kraton 1107 (0.8 kg.) is masticated in a high sheer sigma mixer at 120° C. until soft. To this is added 3.2 kg. of polyisobutylene and mixing is continued until the blend is homogeneous. The mass is cooled to 30° C. at which time the powdered premix is added. Mixing is continued until a homogeneous dough is formed.

This dough mass while hot and soft is extruded and flattened. A sheet of polyethylene 1.5 mils thickness is pressed over one side and silicone coated release paper on the other. The resultant mat is cut into the desired shape.

EXAMPLES 19-25

Following the procedure of Example 18 but employing the following ingredients on a weight percent basis other adhesive compositions within the scope of the invention are prepared.

| Ingredient | Examples | | | | | | |
|---|---|---|---|---|---|---|---|
| | 19 | 20 | 21 | 22 | 23 | 24 | 25 |
| Polyisobutylene (Vistanex LM-MH) | 32 | — | 32 | 32 | — | 32 | — |
| Polyisobutylene (Vistanex LM-MS) | — | 36 | — | — | 36 | — | 36 |
| Guar gum | 25 | 15 | 30 | 25 | — | — | 25 |
| Locust Bean gum | — | — | — | — | — | 20 | — |
| Pectin | — | 15 | — | — | 15 | — | 10 |
| Karaya | — | — | — | — | — | 20 | — |
| Gelatin | — | — | — | — | 15 | — | — |
| Sodium carboxymethylcellulose | 13 | — | — | 12 | 15 | — | — |
| Cross-linked sodium carboxymethylcellulose (Aqualon R) | 12 | 10 | 18 | 13 | — | — | — |
| Starch-acrylonitrile graft copolymer (Grain Processing Corp. Polymer 35-A-100) | — | — | — | — | — | 10 | — |
| Cross-linked dextran (Sephadex CM-C50) | — | — | — | — | — | — | 10 |
| Poly(methylvinyl ether/maleic acid), or its anhydride, or mixed calcium, sodium salt [Gantrez S-97, AN-169, or AT-955] | 10 AT-955 | 15 AT-955 | 12 AT-955 | — | 10 S-97 | 10 AN-169 | 10 AT-955 |
| Gluten | — | — | — | 10 | — | — | — |
| Kraton 1107 | 8 | 9 | 8 | — | — | 8 | 9 |
| Butyl rubber (077) | — | — | — | 8 | — | — | — |
| Polyisobutylene (Vistanex L-100) | — | — | — | — | 9 | — | — |

What is claimed is:

1. An adhesive composition suitable for medical purposes comprising a substantially homogeneous mixture on a percent weight basis of from about 30% to about 70% of a pressure sensitive viscous adhesive material and an optional thermoplastic elastomer said pressure sensitive adhesive material selected from the group consisting of natural rubber, silicone rubber, acrylonitrile rubber, polyurethane rubber, and polyisobutylenes and said optional thermoplastic elastomer selected from the group consisting of medium molecular weight polyisobutylene, butyl rubber, and styrene copolymers and from about 3% to about 60% by weight of one or more natural or synthetic polymers capable of developing elastomeric properties when hydrated selected from the group consisting of gluten and long chain polymers of methyl vinyl ether/maleic acid.

2. An adhesive composition of claim 1 wherein said long chain polymer is selected from the group consisting of poly(methyl vinyl ether/maleic acid), poly(methyl vinyl ether/maleic anhydride), and calcium, sodium poly(methyl vinyl ether/maleic acid).

3. An adhesive composition of claim 2 wherein said pressure sensitive viscous adhesive material is low molecular weight polyisobutylene and said polyisobutylene is present at from about 40% to about 50% by weight of said composition.

4. The adhesive composition of claim 3 consisting essentially of on a weight percent basis of about 40% polyisobutylene and about 60% calcium, sodium poly(methyl vinyl ether/maleic acid).

5. An adhesive composition suitable for medical purposes comprising a substantially homogeneous mixture on a percent weight basis of from about 30% to about 70% of a pressure sensitive viscous adhesive material and an optional thermoplastic elastomer said pressure sensitive viscous adhesive material selected from the group consisting of natural rubber, silicone rubber, acrylonitrile rubber, polyurethane rubber, and polyisobutylenes and said optional thermoplastic elastomer selected from the group consisting of medium molecular weight polyisobutylenes, butyl rubber, and styrene copolymers; from about 3% to about 60% by weight of one or more natural or synthetic polymers capable of developing elastomeric properties when hydrated selected from the group consisting of gluten and long chain polymers of methyl vinyl ether/maleic acid; up to about 50% by weight of one or more water soluble hydrocolloids selected from the group consisting of sodium carboxymethylcellulose, pectin, gelatin, guar gum, locust bean gum, gum karaya, and mixtures thereof; and up to about 30% by weight of one or more water swellable cohesive strengthening agents selected from the group consisting of water insoluble cross-linked sodium carboxymethylcellulose, water insoluble starch-acrylonitrile graft polymer, and water insoluble cross-linked dextran provided that the water soluble hydrocolloids and water insoluble cohesive strengthening agents together are no more than about 60% by weight of said adhesive composition.

6. An adhesive composition of claim 5 wherein said long chain polymer is selected from the group consisting of poly(methyl vinyl ether/maleic acid), poly(methyl vinyl ether/maleic anhydride), and calcium, sodium poly(methyl vinyl ether/maleic acid).

7. An adhesive composition of claim 6 wherein said pressure sensitive viscous adhesive material is low molecular weight polyisobutylene.

8. An adhesive composition suitable for medical purposes comprising a substantially homogeneous mixture on a percent weight basis of from about 40% to about 50% of a pressure sensitive adhesive component comprising low molecular weight polyisobutylene and an optional thermoplstic elastomer selected from the group consisting of medium molecular weight polyisobutylene, butyl rubber, and styrene-isoprene-styrene copolymers; from about 10% to about 35% of a polymer selected from the group consisting of poly(methyl vinyl ether/maleic acid), poly(methyl vinyl ether/maleic anhydride), and calcium, sodium poly(methyl vinyl ether/maleic acid); from about 15% to about 40% of one or more water soluble hydrocolloids selected from the group consisting of sodium carboxymethylcellulose, pectin, gelatin, guar gum, locust bean gum, gum karaya, and mixtures thereof; and up to about 30% of one or more water swellable cohesive strengthening agents selected from the group consisting of water insoluble cross-linked sodium carboxymethylcellulose, water insoluble starch-acrylonitrile graft copolymer, water insoluble cross-linked dextran, and mixtures thereof provided that the water soluble hydrocolloids and water swellable cohesive strengthening agents together are no more than about 55% by weight of said composition.

9. An adhesive composition of claim 8 wherein said water soluble hydrocolloids are selected from the group consisting of guar gum, sodium carboxymethylcellulose, and mixtures thereof and said cohesive strengthening agent if present is cross-linked sodium carboxymethylcellulose.

10. The adhesive composition of claim 9 consisting essentially of on a percent weight basis of about 40% low molecular weight polyisobutylene, about 25% guar gum, about 10% sodium carboxymethylcellulose, about 15% cross-linked sodium carboxymethylcellulose, and about 10% calcium, sodium poly(methyl vinyl ether/maleic acid).

11. The adhesive composition of claim 9 consisting essentially of on a weight percent basis of about 40% low molecular weight polyisobutylene, about 25% guar gum, about 10% sodium carboxymethylcellulose, about 15% cross-linked sodium carboxymethylcellulose, and about 10% poly(methyl vinyl ether/maleic acid).

12. The adhesive composition of claim 9 consisting essentially of on a percent weight basis of about 40% low molecular weight polyisobutylene, about 30% sodium carboxymethylcellulose, and about 30% calcium, sodium poly(methyl vinyl ether/maleic acid).

13. The adhesive composition of claim 9 consisting essentially of on a weight percent basis of about 40% low molecular weight polyisobutylene, about 30% guar gum, and about 30% calcium, sodium poly(methyl vinyl ether/maleic acid).

14. The adhesive composition of claim 9 consisting essentially of on a weight percent basis of about 40% low molecular weight polyisobutylene, about 17.2% sodium carboxymethylcellulose, about 25.6% cross-linked sodium carboxymethylcellulose, and about 17.2% calcium, sodium poly(methyl vinyl ether/maleic acid).

15. A skin barrier comprising an adhesive layer having a thin continuous or discontinuous polymeric film laminated to one surface of the adhesive, said adhesive comprising a substantially homogeneous mixture on a percent weight basis of from about 30% to about 70% of a pressure sensitive viscous adhesive material and an optional thermoplastic elastomer said pressure sensitive adhesive material selected from the group consisting of natural rubber, silicone rubber, acrylonitrile rubber, polyurethane rubber, and polyisobutylenes and said optional thermoplastic elastomer selected from the group consisting of medium molecular weight polyisobutylenes, butyl rubber, and styrene copolymers and from about 3% to 60% by weight of one or more natural or synthetic polymers capable of developing elastomeric properties when hydrated selected from the group consisting of gluten and long chain polymers of methyl vinyl ether/maleic acid.

16. A skin barrier of claim 15 wherein said long chain polymer is selected from the group consisting of poly(methyl vinyl ether/maleic acid), poly(methyl vinyl ether/maleic anhydride), and calcium, sodium poly(methyl vinyl ether/maleic acid).

17. A skin barrier of claim 16 wherein said pressure sensitive viscous adhesive material is low molecular weight polyisobutylene and said polyisobutylene is present at from about 40% to about 50% by weight of said composition.

18. A skin barrier of claim 17 wherein said adhesive layer consists essentially of on a weight percent basis of about 40% polyisobutylene and about 60% calcium, sodium poly(methyl vinyl ether/maleic acid).

19. A skin barrier of claim 15 wherein said polymeric film is polyethylene.

20. A skin barrier comprising an adhesive layer having a thin continuous or discontinuous polymeric film laminated on one surface of the adhesive, said adhesive comprising a substantially homogeneous mixture on a percent weight basis of from about 30% to about 70% of a pressure sensitive viscous adhesive material and an optional thermoplastic elastomer said pressure sensitive adhesive material selected from the group consisting of natural rubber, silicone rubber, acrylonitrile rubber, polyurethane rubber, and polyisobutylenes and said optional thermoplastic elastomer selected from the group consisting of medium molecular weight polyisobutylenes, butyl rubber, and styrene compolymers; from about 3% to about 60% by weight of one or more natural or synthetic polymers capable of developing elastomeric properties when hydrated selected from the group consisting of gluten and long chain polymers of methyl vinyl ether/maleic acid; up to about 50% by weight of one or more water soluble hydrocolloids selected from the group consisting of sodium carboxymethylcellulose, pectin, gelatin, guar gum, locust bean gum, gum karaya, and mixtures thereof; and up to about 30% by weight of one or more water swellable cohesive strengthening agents selected from the group consisting of water insoluble cross-linked sodium carboxymethylcellulose, water insouble starch-acrylonitrile graft copolymer, and water insoluble cross-linked dextran provided that the water soluble hydrocolloids and water insoluble cohesive strengthening agents together are no more than about 60% by weight of said adhesive composition.

21. A skin barrier of claim 20 wherein said long chain polymer is selected from the group consisting of poly(methyl vinyl ether/maleic acid), poly(methyl vinyl ether/maleic anhydride), and calcium, sodium poly(methyl vinyl ether/maleic acid).

22. A skin barrier of claim 21 wherein said pressure sensitive viscous adhesive material is low molecular weight polyisobutylene.

23. A skin barrier of claim 20 wherein said polymeric film is polyethylene.

24. A skin barrier comprising an adhesive layer having a thin continuous or discontinuous olymeric film laminated to one surface of the adhesive, said adhesive comprising a substantially homogeneous mixture on a percent weight basis of from about 40% to about 50% of a pressure sensitive adhesive component comprising low molecular weight polyisobutylene and an optional thermoplastic elastomer selected from the group consisting of medium molecular weight polyisobutylene, butyl rubber, and styrene-isoprenestyrene copolymers; from about 10% to about 35% of a polymer selected from the group consisting of poly(methyl vinyl ether/maleic acid), poly(methyl vinyl ether/maleic anhydride), and calcium, sodium poly(methyl vinyl ether/maleic acid); from about 15% to about 40% of one or more water soluble hydrocolloids selected from the group consisting of sodium carboxymethylcellulose, pectin, gelatin, guar gum, locust bean gum, gum karaya, and mixtures thereof; and up to about 30% of one or more water swellable cohesive strengthening agents selected from the group consisting of water insoluble cross-linked sodium carboxymethylcellulose, water insoluble startch-acrylonitrile graft copolymer, water insoluble cross-linked dextran, and mixtures thereof provided that the water soluble hydrocolloids and water swellable cohesive strengthening agents together are no more than about 55% by weight of said composition.

25. A skin barrier of claim 24 wherein said water soluble hydrocolloids are selected from the group consisting of guar gum, sodium carboxymethylcellulose, and mixtures thereof and said cohesive strengthening agent if present is cross-linked sodium carboxymethylcellulose.

26. A skin barrier of claim 25 wherein said adhesive layer consists essentially of on a percent weight basis of about 40% low molecular weight polyisobutylene, about 25% guar gum, about 10% sodium carboxymethylcellulose, about 15% cross-linked sodium carboxymethylcellulose, and about 10% calcium, sodium poly(methyl vinyl ether/maleic acid).

27. A skin barrier of claim 25 wherein said adhesive layer consists essentially of on a percent weight basis of about 40% low molecular weight polyisobutylene, about 25% guar gum, about 10% sodium carboxymethylcellulose, about 15% cross-linked sodium carboxymethylcellulose, and about 10% poly(methyl vinyl ether/maleic acid).

28. A skin barrier of claim 25 wherein said adhesive layer consists essentially of on a percent weight basis of about 40% low molecular weight polyisobutylene, about 30% sodium carboxymethylcellulose, and about 30% calcium, sodium poly(methyl vinyl ether/maleic acid).

29. A skin barrier of claim 25 wherein said adhesive layer consists essentially of on a weight percent basis of about 40% low molecular weight polyisobutylene, about 30% guar gum, and about 30% calcium, sodium poly(methyl vinyl ether/maleic acid).

30. A skin barrier of claim 25 wherein said adhesive layer consists essentially of on a weight percent basis of about 40% low molecular weight polyisobutylene, about 17.2% sodium carboxymethylcellulose, about 25.6% cross-linked sodium carboxymethylcellulose, and about 17.2% calcium, sodium poly(methyl vinyl ether/maleic acid).

31. A skin barrier of claim 24 wherein said polymeric film is polyethylene.

* * * * *